United States Patent [19]

Suddith

[11] Patent Number: 5,556,580
[45] Date of Patent: Sep. 17, 1996

[54] LIPOSOME CONTINUOUS SIZE REDUCTION METHOD AND APPARATUS

[75] Inventor: Robert L. Suddith, Robbinsville, N.J.

[73] Assignee: The Liposome Company, Inc., Princeton, N.J.

[21] Appl. No.: 437,906

[22] Filed: May 10, 1995

Related U.S. Application Data

[63] Continuation of Ser. No. 132,159, Oct. 5, 1993, abandoned, which is a continuation of Ser. No. 576,174, Aug. 30, 1990, abandoned, which is a continuation of Ser. No. 36,980, Apr. 16, 1987, abandoned.

[51] Int. Cl.$^6$ .............. A61K 9/127; B01J 13/20; B28B 1/54
[52] U.S. Cl. .............. 264/4.3; 264/4.1; 424/450; 425/5; 436/829
[58] Field of Search ............ 264/4.1, 4.3; 436/829; 424/450; 425/5; 241/3, 95, 274

[56] References Cited

U.S. PATENT DOCUMENTS

| | | | |
|---|---|---|---|
| 4,016,100 | 4/1977 | Suzuki et al. | 264/4.3 |
| 4,235,871 | 11/1980 | Papahadjopoulos et al. | 424/450 |
| 4,372,949 | 2/1983 | Kodama et al. | 424/450 |
| 4,394,372 | 7/1983 | Taylor | 424/85 |
| 4,429,008 | 1/1984 | Martin et al. | 428/402.2 |
| 4,460,577 | 7/1984 | Moro et al. | 424/450 |
| 4,515,736 | 5/1985 | Deamer | 264/4.3 |
| 4,522,803 | 6/1985 | Lenk et al. | 424/1.1 |
| 4,529,561 | 7/1985 | Hunt et al. | 264/4.3 |
| 4,619,795 | 10/1986 | Cohen | 264/4.6 |
| 4,737,323 | 4/1988 | Martin et al. | 264/4.3 |
| 4,752,425 | 6/1988 | Martin et al. | 264/4.6 |
| 4,781,871 | 11/1988 | West, III et al. | 264/4.3 |
| 4,861,580 | 8/1989 | Janoff et al. | 424/1.1 |
| 5,008,050 | 4/1991 | Cullis et al. | 264/4.3 |
| 5,180,713 | 1/1993 | Abra et al. | 424/450 X |

FOREIGN PATENT DOCUMENTS

| | | |
|---|---|---|
| 0036676 | 9/1981 | European Pat. Off. . |
| 8312550 | 2/1985 | France . |
| 2820057 | 11/1979 | Germany . |
| 1173179 | 12/1969 | United Kingdom .............. C23B 3/02 |
| 85/00968 | 3/1985 | WIPO . |
| 86/00238 | 1/1986 | WIPO . |
| 87/00043 | 1/1987 | WIPO . |

OTHER PUBLICATIONS

Bangham, et al., "Diffusion of Univalent Ions Across the Lamellae of Swollen Phospholipids", 1965, J. Mol. Bio. 13:238–252.

Grant & Hackh's Chemical Dictionary, Fifth Edition, McGraw–Hill Book Company, New York (1987), pp. 228 and 235.

Hope, et al., "Production of Large Unilamellar Vesicles by a Rapid Extrusion Produce, Characterization of size distribution trapped volume and ability to maintain a membrane potention" Biochem. Biophys. Acta, 812(1), 55–65, 1985.

Materials Handbook, Eighth Edition, Brady, pp. 780–781 (1956).

Mayer, et al., "Solute Distributions and Trapping Efficiencies Observed in Freeze–Thawed Multilamellar Vesicles", 1985, Biochim. et Biophys. Acta, 9817:193–196.

Papahadjopoulos, et al., "Phospholipid Model Membranes I. Structural Characteristics of Hydrated Lipid Crystals", 1967, BBA 135:624–6389.

Van Nostrand's Scientific Encyclopedia, Seventh Edition, Van Nostrand Peinhold Book Co., New York (1989), p. 1107.

The Random House College Dictionary (1980), p. 1049.

Primary Examiner—Richard D. Lovering
Attorney, Agent, or Firm—Kenneth B. Rubin

[57] ABSTRACT

A method of extruding liposomes from liposomal material comprising extruding the liposomal material through a frit, and apparatus for extrusion.

10 Claims, 3 Drawing Sheets

LIPOSOME CONTINUOUS SIZE REDUCTION METHOD AND APPARATUS

This application is a continuation of U.S. Ser. No. 08/132,159, filed Oct. 5, 1993 and now abandoned, which is a continuation of U.S. Ser. No. 07/576,174, filed Aug. 30, 1990 and now abandoned, which-in-turn is a continuation of U.S. Ser. No. 07/036,980, filed Apr. 16, 1987 and now abandoned.

FIELD OF THE INVENTION

Liposomes comprise a class of bilayer lipid structures with a host of applications, particularly in the pharmaceutical arts. A number of distinct liposomal structures have been identified such as stable plurilamellar vesicles (U.S. Pat. No. 4,522,803) multilamellar vesicles (Bangham et al., 1960 *J. Mol. Biol.* 13:238–252), and reverse-phase evaporation vesicles (U.S. Pat. No. 4,235,871). Particularly of interest are unilamellar vesicles as described by Papahadjapolous and Miller in *Biochim. Biophys. Acta.* 135:624–638 (1967).

Frozen and thawed multilamellar vesicles (FATMLV) are described in "Solute Distributions and Trapping Efficiencies Observed in Freeze-Thawed Multilamellar Vesicles," Mayer et al., *Biochima et Biophysica Acta.* 817:193–196 (1985), the teachings of which are herein incorporated by reference.

A problem encountered in the liposome art is size variability of the liposomes. Size uniformity is a particular consideration in the pharmaceutical use of liposomes for injection. Injected liposomes of over about 5 microns (5000 nanometers) in diameter may block capillaries. Liposomes of uniform size will have both predictable and selectable distribution characteristics. This invention concerns an improved method and apparatus for achieving uniform liposome size.

BACKGROUND OF THE INVENTION

The filtration and extrusion of liposomes directed to achieving liposome preparations of uniform size are known in the art. However, filtration/extrusion rates have been low being no higher than about 12 ml/minute.

Hunt and Papahadjopolous disclose a "Method for Producing Liposomes in Selected Size Ranges" in U.S. Pat. No. 4,529,561 ("Hunt") by a filtration/extrusion process.

The Hunt process is described either as one of extruding liposomes under pressure through a "uniform-pore-size membrane" or forcing liposomes "through an orifice under pressure." The Hunt filtration-extrusion membrane process is further distinguished in Hunt from the orifice process as being performed at lower pressure. In practice, the membrane process is associated with the retention or buildup of material on the input surface of the filtration-extrusion membrane. This build up reduces flow while requiring increased driving pressure.

Suzuki et al. (U.S. Pat. No. 4,016,100) describes a liposomal preparation with a filtration step utilizing a membrane filter. In Suzuki et al. it is also noted that the liposomes are formed in a uniform size. The filtration process of Suzuki et al. further has a limited through-put capacity due to pressure limitation of membranes and the membrane occlusion that arises from material buildup on the membrane input surface.

It is an object of this invention to provide a method of extruding liposomes to provide smaller liposome sizes.

It is another object of this invention to provide a method of producing liposomes of uniform size from liposomal material.

It is an additional object of this invention to provide a high speed/high volume method of continuous size reduction of liposomes.

SUMMARY OF THE INVENTION

The instant invention provides a method of extruding liposomes into smaller sized more uniform populations from liposomal material by extruding the liposomal material through a frit without use of a membrane. Also provided is an extrusion apparatus for such extrusion. This method is extrusion without filtration in that substantially all of material presented to the extruder is passed through.

Critical to this invention is the discovery that the use of a frit as an extruder element will extrude liposomes into a uniform population of reduced size without frit occlusion while affording substantially total through-put of liposomal material.

As a frit is not a uniform-pore-size element, frit porosity is expressed as a pore size designation. Preferred are frits of pore size designations of 500 nanometers as well as frits of smaller pore size designations. These frits are described herein as having pore size designations of 500 nanometers or less. Using a single frit produces the desired result of producing uniform populations of size reduced liposome and has the advantages of structural strength and simplicity. The structural strength of a frit permits use of operating pressures for extrusion far in excess of those that may be used in a membrane filtration/extrusion system. The use of frits of decreasing pore size designations is not required.

The invention includes a method of extruding liposomal material by passing the liposomal material through a frit. The invention further includes extrusion of substantially all liposomal material. This method also includes preparing the liposomal material into liposomes prior to extrusion. The invention further includes using a frit with a pore size designation of about 500 nanometers or less. The method additionally includes passing the liposomal material through the frit under pressure. Preferred pressures are in excess of about 100 pounds per square inch. Pressures of about 1000 psi or greater are more preferred. Extrusion at rates of 10 ml of liposomal material/minute/cm$^2$ of frit surface area and up to 40 ml/minute/cm$^2$ are further included in this invention.

The method further includes repeatedly passing liposomal material through the frit. Preferred is a method of at least about 3 passes. More preferred is a method of at least 10 passes through the frit. The method further includes the step of preparing the liposomal material in nonliposomal form (such as by mere dispersal of said materials in a liquid phase) prior to the step of passing the liposomal material through the frit.

The foregoing methods are preferably performed using a metal frit.

The apparatus for extruding liposomes of this invention includes a reservoir suitable for containing liposomal material in communication with a pump being in connection with a frit.

The apparatus additionally includes a frit, preferably a metal frit, of a pore size designation of about 500 nanometers or less. The apparatus further includes a pump which functions at an operating pressure of at least about 100 pounds per square inch.

DETAILED DESCRIPTION OF THE INVENTION

Figure 1:
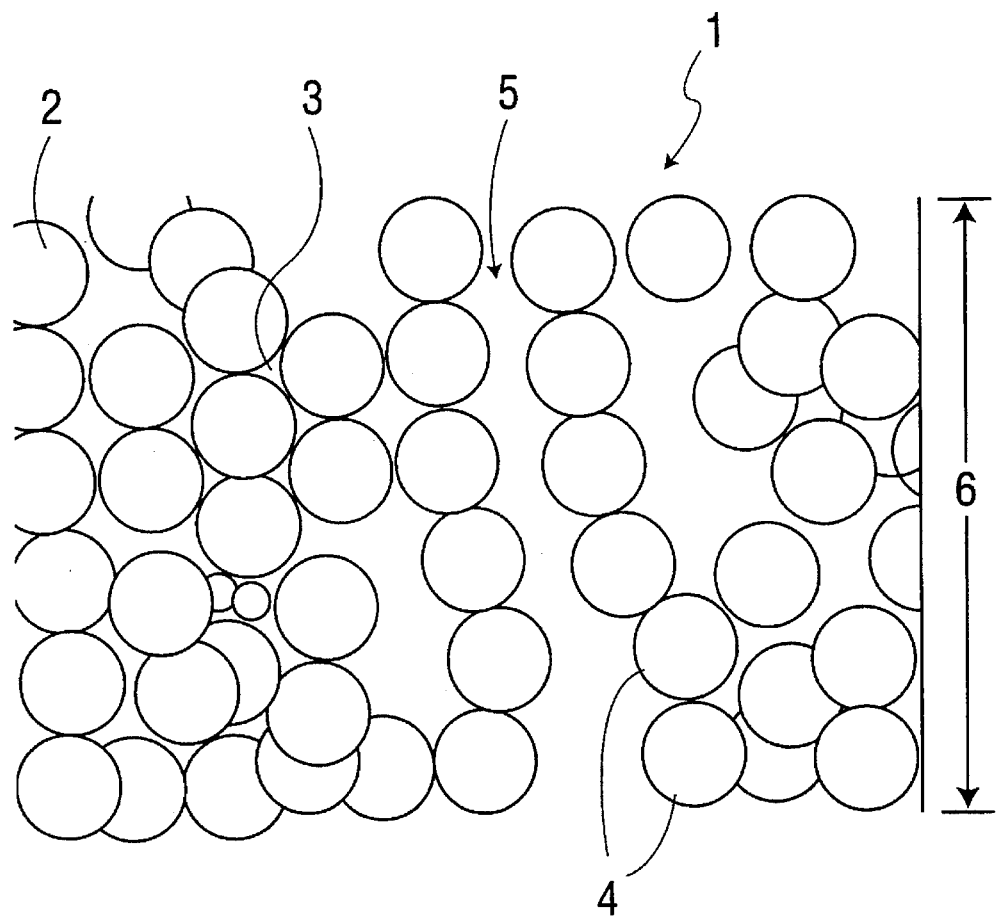
FIG. 1 is a diagramatic side plan of an enlarged section of a frit in cutaway.

High speed/high volume extrusion of liposomes with substantially total through-put of starting liposomal material (lipid, aqueous phase, and optionally organic solvents and/or bioactive agent) is achieved by passage of such starting liposomal material through a frit. As used herein the term liposome referring to extruded product includes both lipid and lipid-drug aggregates as well as true liposomes.

The term lipid as used herein shall mean any suitable material resulting in a bilayer such that a hydrophobic portion of the lipid material orients toward the bilayer while a hydrophilic portion orients toward the aqueous phase. Lipids include highly hydrophobic compounds such as triglycerides, sterols such as cholesterol and amphipathic lipids.

Of this broad group of lipids, amphipathic lipids are utilized as the primary liposomal structural element in the practice of this invention. The amphipathic lipids have the property of having a polar (hydrophilic) moiety and a hydrophobic moiety. Hydrophilic character could be imparted to the amphipathic lipids molecule through the presence of phosphato, carboxylic, sulphato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group. The preferred amphipathic compounds are phosphoglycerides, representative examples of which include phosphatidylcholine, phosphatidylethanolamine, phosphatidylserine, phosphatidylinositol, phosphatidic acid and diphosphatidylglycerol. Synthetic-saturated compounds such as dimyristoylphosphatidylcholine, dipalmitoylphosphatidylcholine, dimyristoylphosphatidylglycerol, or distearoylphosphatidylcholine or unsaturated species such as dioleoylphosphatidylcholine or dilinoleoylphosphatidylcholine are also usable. Other compounds lacking phosphorous, such as members of the sphingolipid and glycosphingolipid families, are also within the group designated as amphipathic lipid.

The amphipathic lipids may be utilized admixed with other lipids including triglycerides and sterols.

As used herein liposomal material whether in the form of liposomes or in a mixture of liposome constituents in nonliposomal form comprises any constituents that form or associate with liposomes. Liposomal material will be understood to include lipids, aqueous media, and optionally organic solvents and bioactive agents.

Liposomal material further includes, under certain circumstances, surfactants and other dispersants that will suspend lipids. Suitable organic solvents are those with a variety of polarities and dielectric properties, which solubilize lipids, include but are not limited to chloroform, methanol, dimethylsulfoxide, methylene chloride, and solvent mixtures such as benzene:methanol. A representative surfactant is an octoxynol such as Triton X-100 (Rohm & Haas). Water, 0.9% saline, as well as citrate or phosphate buffers may also function as lipid dispersants. In some instances, water soluble organic solvents, such as ethanol, will be present in the aqueous phase. Suitable solvents or surfactants or dispersants are those which will distribute lipid throughout a solution and are preferably chosen on the basis of biocompatibility, toxicity, and flammability.

Biologically active agents ("bioactive agent") as used herein include but are not limited to antibacterial compounds such as gentamycin, antiviral agents such as rifampacin, antifungal compounds such as amphotericin B, anti-parasitic compound such as antimony derivatives, tumoricidal compounds such as adriamycin, anti-metabolites, peptides, proteins such as albumin, toxins such as diptheriatoxin, enzymes such as catalase, polypeptides such as cyclosporin A, hormones such as estrogen, hormone antagonists, neurotransmitters such as acetylcholine, neurotransmitter antagonists, glycoproteins such as hyaluronic acid, lipoproteins such as alpha-lipoprotein, immunoglobulins such as IgG, immunomodulators such as interferon or interleukin, vasodilators, dyes such as Arsenazo III, radiolabels such as $^{14}C$, radio-opaque compounds such as $^{90}Te$, fluorescent compounds such as carboxy fluorescein, receptor binding molecules such as estrogen receptor protein, anti-inflammatories such as indomethacin, antiglaucoma agents such as pilocarpine, mydriatic compounds, local anesthetics such as lidocaine, narcotics such as codeine, vitamins such as alpha-tocopherol, nucleic acids such as thymine, polynucleotides such as RNA polymers, psychoactive or anxiolytic agents such as diazepam, mono-di- and polysaccharides, etc. A few of the many specific compounds that can be entrapped are pilocarpine, a polypeptide growth hormone such as human growth hormone, bovine growth hormone and porcine growth hormone, indomethacin, diazepam, alpha-tocopherol itself and tylosin. Antifungal compounds include miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole and ciclopirox alemine, preferably miconazole or terconazole. The entrapment of two or more compound simultaneously may be especially desirable where such compounds produce complementary or synergistic effects. The amounts of drugs administered in liposomes will generally be the same as with the free drug; however, the frequency of dosing may be reduced.

High speed/high volume extrusion as a function of the surface of the extruding element (here a frit) as used herein refers to extrusion rates over about 10 ml/minute/cm$^2$ frit surface area and preferably over about 20 ml/minute/cm$^2$ and most preferably over about 40 ml/minute/cm$^2$ or greater. With a frit of 2.5 cm$^2$ surface area these rates of extrusion are 25, 50, and 100 ml/minute respectively. High speed/high volume is also expressed as high rate extrusion.

A frit element as used herein is a structural member comprised of generally bead-like material partially conjoined, usually by compression and/or sintering. Among the many materials useful in frit preparation are ceramic, glass metal and metal/carbide bead-like materials which are conjoined into a frit. Due to the low affinity of lipid for metal, metal frits are preferred for facilitating substantially total through-put of material. The preferred metal frit is of stainless steel.

Frits are available from a number of sources such as Ace Scientific Company, (East Brunswick, N.J.), Scientific Systems, Inc.(State College, Penn.) and Ranin Instrument Company (Woburn, Mass.). Frits are characterized in having nonuniform pore size over a pore size range. Frit pore size range is experimentally determined on the basis of material that passes through or is excluded by the frit. This defines a range of particle sizes a portion of which lie above and below, the stated pore size. As used herein frit pore size of a frit will be referred to as a pore size "designation" based upon such an empirical tests well known in the art. Paths through the frit are not straight paths and path walls are irregular. Frits may be prepared in a number of shapes including rod or disc shapes.

The detailed section of a frit 1 used in this invention is depicted in detailed cut away side view in FIG. 1 and comprises a matrix of essentially solid subunits 2 partially sintered together leaving interstitial spaces 3. Sintered subunits form a partially continuous surface 4 yielding non-straight path trans-frit openings 5. The partial continuity of surface is sufficiently continuous such that the frit strength is a function of the length of its cross sectional axis 6 Frits are conveniently about 2 cm in diameter and about 0.1 cm thick, but these dimensions are not critical. Frits as large as 20 cm in diameter or larger, may be utilized. Frits in rod shape are useful including those of about 10 inches in length and about 1 inch in diameter. Preferred frits have a pore size designation of about 500 nm down to those of about 200 nm. Frits of a pore size designation of about 100 nm or less tend to be of prohibitively high resistance to flow and are not preferred for this application.

Figure 2:
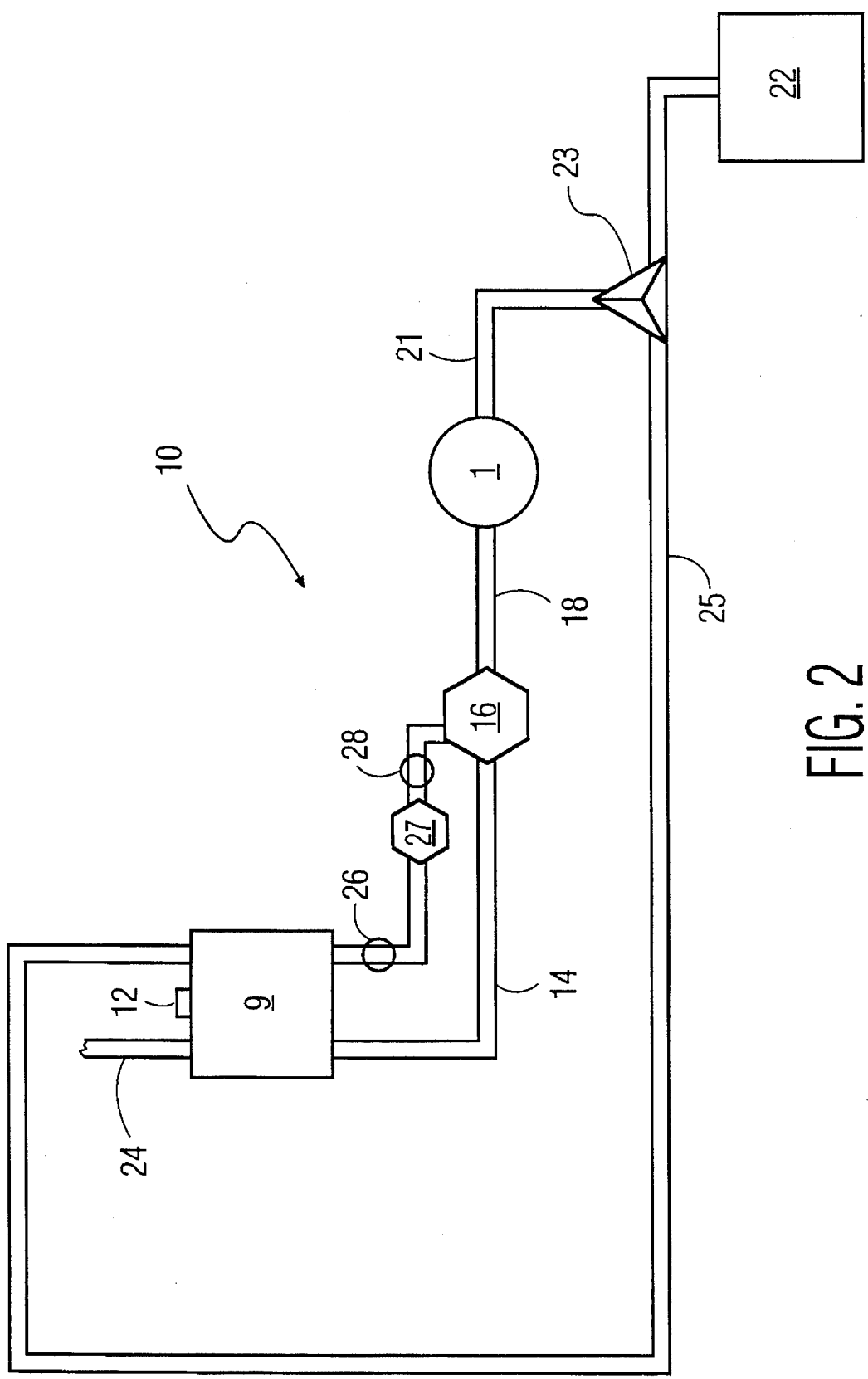
FIG. 2 is a diagramatic plan of the extrusion apparatus of the present invention.

FIG. 2 depicts the preferred extrusion apparatus 10 with a feed reservoir 9 for liposomal material with a capped access port 12. The input reservoir is connected through line 14 to a pump 16 leading through line 18 to frit 1, positioned in-line. The liposome material pumped through the frit passes through line 21 and through 3-way valve 23 and is received into collection vessel 22 collecting extruded material. Line 24 entering into input reservoir 9 may be used to degas the liposomal material if connected to a vacuum source, pressurize the liposomal material if connected to a pressure source, or direct a particular gas such as nitrogen to the liposomal material. Return line 25 from three-way valve 23 into the feed reservoirs permits the recycling of extruded material.

In using this apparatus the lipid material may be introduced to the pump 16 by any pump means known to the art. When piston pumps are employed, liposomal material may be drawn into the pump head itself. External pumping of feed stock from the feed reservoir 9 by an external pumping device 27 and a first two-way valve 26 and a second two-way valve 28 deliver feed stock to pump 16. The pump head then provides energy for circulation of the liposomal material through the frit. The invention is not limited to piston pumps and any suitable pumping means may be used including diaphragm pumps. In embodiments with a sufficient hydrostatic head and thus a sufficient trans-frit pressure differentail the pump is not necessary.

Figure 3:
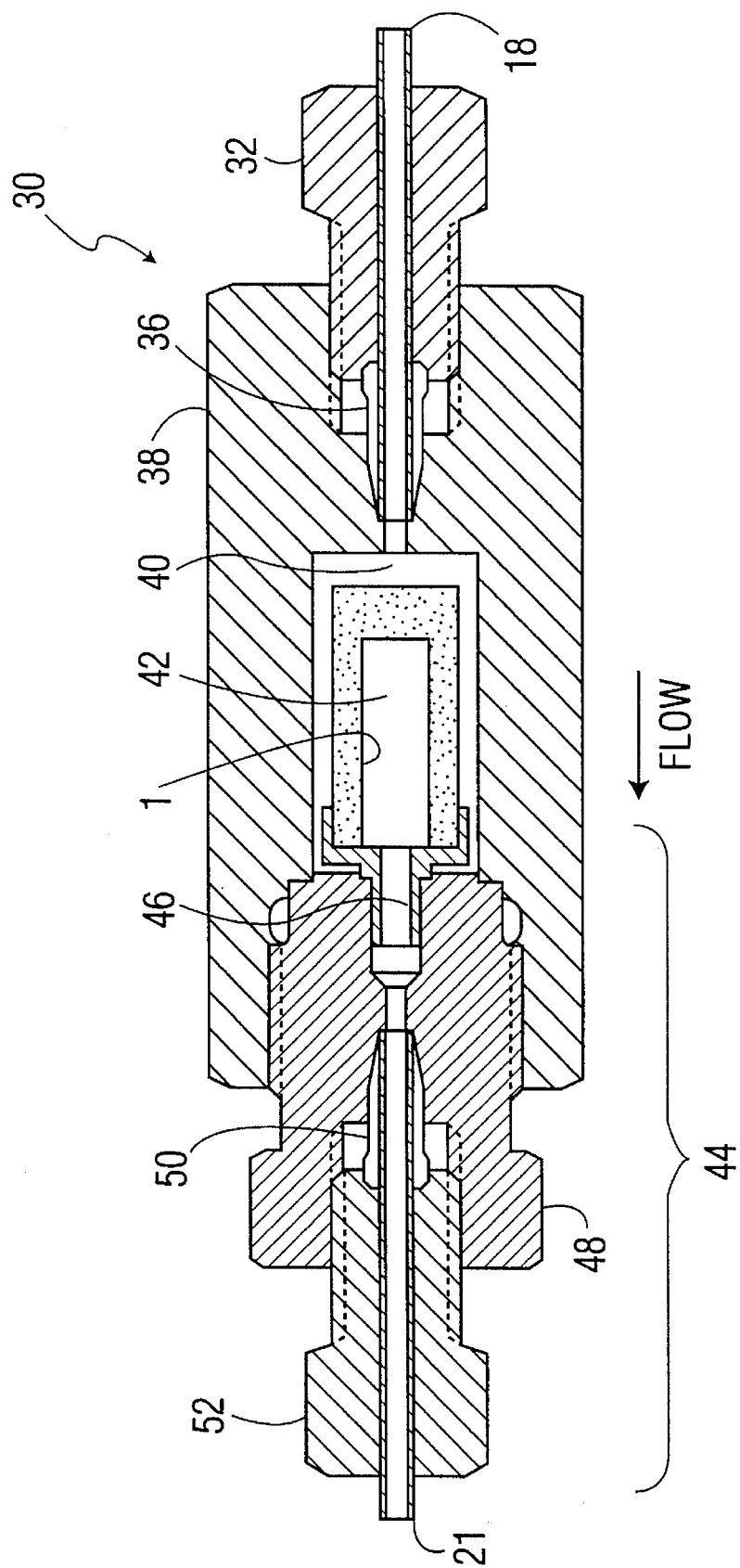
FIG. 3 is a diagramatic side plan of a frit with flow fittings in cutaway.

FIG. 3 is a diagramatic side plan of a frit with flow fittings 30. With such fittings a frit is placed in-line in the apparatus of this invention. Liposomal material is pumped through line 18 fixed in pressure tight connection to vessel 38 by primary entry fitting 34 and secondary entry fitting 36. Liposomal material enters chamber 40 and is extruded through frit 1 into space 42 and is removed through line 21. Line 21 is fixed in pressure tight connection to frit 1 in vessel 38 by exit fitting assembly 44 comprised of frit seat 46, primary exit fitting 48 secondary exit fitting 50 and tertiary exit fitting 52.

The high rate of extrusion is enabled by the strength of the frit, which does not suffer occlusion and is not deformed by the pressure of the extrusion step. Membrane type extrusion is rate limited by the minimal resistance to deformation of membrane material. The frit extrusion rate is primarily limited by the pumping pressure. Pressures of over 200 psi are preferred with about 1000 psi or more most preferred. A preferred pump is the Ranin Rabbit HPX, a piston type pump. Pumps may be utilized at pressures of from about 50 psi and higher.

While the trans-frit pressure will be the primary determinant of the extrusion rate, other factors such as fluid viscosity will affect the extrusion rate. Those skilled in the art will understand that at smaller frit pore size designations liposomal materials of lesser viscosity are preferred. Further if the frit material is lipophilic, lipid adhesion to the frit may compromise frit pore size.

It is an advantage of this invention that a single frit may be utilized to accomplish the extrusion of this invention.

The invention will be better understood by reference to the following examples, while not being limited thereby:

EXAMPLE 1

Preparation of Liposomal Material and Extrusion

Liposomal material was prepared by stirring 100 gm of egg phosphatidylcholine into 1000 gm of methylene chloride at ambient temperature and pressure. Next 1000 gm of 0.9% saline containing 100 mg/ml streptomycin was added with stirring. The methylene chloride was removed by evaporation and the resulting liposomal material was comprised of liposomes with a mean diameter of 0.54 micron.

50 ml of the resulting liposomal material was placed in a feed reservoir. This feed reservoir was connected to a piston pump (Ranin Rabbit HPX) equipped with a 25 ml/minute preparative pump head. This pump was in fluid connection with a stainless steel frit (Scientific Systems, Inc.) with a pore size designation of 500 nanometer. The frit was 5 mm in diameter and 0.7 mm thick.

The 50 ml of the resulting liposomal material was extruded at a rate of 25 ml/minute with the contents extruded 3 times through the frit. Total recovery of the material was not less than 99.99%. After each pass through the frit the mean diameter of the extruded liposomes was determined by quasi-elastic light scattering methodology. The results are shown in Table 1. A mean liposome diameter of 0.27 micron was achieved. The extrusion of the liposomes yielded a reduction in liposome size from a mean diameter 0.54 micron size to an mean diameter of 0.27 micron. Thus the extrusion method yielded a 50% reduction in liposome size.

EXAMPLE 2

Extrusion of Liposomal Material

Liposomal material was prepared by the method of Example 1 but utilizing amikacin instead of streptomycin. Next 300 ml of the resulting liposomal material was pumped through a frit with 500 nanometer pore size designation as in Example 1. Four passes through the frit were made with the results shown in Table 2. The starting liposomal material had a mean diameter of 0.41 micron and after extrusion a mean diameter of 0.18 microns. This extrusion represents a reduction in liposome size of over 50%.

EXAMPLE 3

Preparation and Extrusion: Pilocarpine-Alpha Tocopherol Hemisuccinate

Five grams of pilocarpine base were added to a weighed 500ml round bottom flask and stopper, and the total mass in grams recorded. D-alpha-tocopherol acid succinate (12.75 g, corresponding to a 1:1 M ratio of pilocarpine:D-alpha-tocopherol) was added to the flask and the contents again weighed. Methylene chloride (50 ml) was added and the flask agitated to dissolve the solids and the flask again weighed. The flask was placed on a rotary evaporator in a water bath at 55° C. and rotated for 30 minutes (no vacuum applied). After 30 minutes, the flask and contents were again weighed, then rotary evaporated with vacuum at 55° C. The weight of the flask was recorded every 30 minutes thereafter until two successive weighings were within 0.1 g. The preparation was then cooled to room temperature (25° C.), stoppered, and stored at 4° C.

The 500 ml round bottom flask containing the pilocarpine-D-alpha tocopherol was placed on a rotary evaporator; with the water bath temperature set at 55° C. The material was warmed for 30 minutes, then the water bath temperature reduced to 35° C. An aqueous solution of 0.1% (w/v) sorbic acid 0.1% (w/v) sodium EDTA dihydrate (92 ml) was added and the suspension vortically mixed. The final volume was adjusted to 125 ml with additional aqueous phase. The resulting liposomes were extruded 10 times as in Example 1 producing size-reduced liposomes having a uniform average mean diameter.

EXAMPLE 4

Preparation and Extrusion: Pilocarpine-Alpha-Tocopherol Hemisuccinate

The materials and procedures of Example 3 were followed using a 5.0 liter round bottom flask and stopper, 30 g of pilocarpine base, 76.5 g of D-alpha-tocopherol acid succinate (corresponding to a 1:1 M ratio of pilocarpine:D-alpha-tocopherol), and 300 ml of methylene chloride.

The 5 liter round bottom flask containing the pilocarpine-D-alpha tocopherol was placed on a rotary evaporator; with the water bath temperature set at 55° C. The mixture was warmed for 30 minutes, then the water bath temperature was reduced to 35° C. An aqueous solution of 0.01% (w/v) sorbic acid with 0.01% (w/v) disodium EDTA dihydrate (550 ml) was added and the suspension mixed for 1–1.5 hours using an agitator blade. The final volume was adjusted to 750 ml with additional aqueous phase. The resulting liposomes were processed by method of Example 1 passing the liposomes 10 times through a stainless steel frit having a nominal pore size designation of 500 nm.

TABLE 1

| Passage No. | Mean Diameter (microns) | % Size Reduction |
| --- | --- | --- |
| 0 | 0.54 | — |
| 1 | 0.38 | 30 |
| 2 | 0.35 | 36 |
| 3 | 0.27 | 50 |

TABLE 2

| Passage No. | Mean Diameter (microns) | % Size Reduction |
| --- | --- | --- |
| 0 | 0.41 | — |
| 1 | 0.34 | 17 |
| 2 | 0.29 | 29 |
| 3 | 0.26 | 35 |
| 4 | 0.18 | 57 |

I claim:

1. A method of producing size reduced liposomes in the absence of a filter membrane comprising passing the liposomes through a non-uniform pore size frit having a pore size designation of from at least about 100 nm to about 500 nm, wherein the passage is under a continuous pressure of greater than about 100 pounds per square inch and at a flow rate of at least about 10 ml/minute/cm$^2$ frit surface area, and wherein substantially all of the size-reduced liposomes have a diameter less than the pore size designation of the frit.

2. The method of claim 1 wherein the frit is comprised of metal.

3. The method of claim 1 wherein the rate is at least about 40 ml/minute/cm$^2$ frit surface area.

4. The method of claim 1 wherein the pressure is at least about 200 pounds per square inch.

5. The method of claim 1 comprising the steps of passing the liposomes through the frit at least about 3 times.

6. The method of claim 5 comprising the steps of passing the liposomes through the frit at least about 10 times.

7. The method of claim 1 wherein the liposomes are comprised of a phospholipid.

8. The method of claim 7 wherein the phospholipid comprises a phosphatidylcholine.

9. The method of claim 8 wherein the phosphatidylcholine comprises egg phosphatidylcholine.

10. An apparatus for producing size-reduced liposomes in accordance with the method of claim 1 which comprises:

(a) A feed reservoir suitable for containing a liposome suspension;

(b) a non-uniform pore size frit having a pore size designation of from at least about 100 nm to about 500 nm; and (c) a pump operably connected to the reservoir and the frit, wherein the pump is capable of operating at a pressure of at least about 100 pounds per square inch.

* * * * *